United States Patent [19]

Fuchs et al.

[11] 4,118,387
[45] Oct. 3, 1978

[54] NAPHTHALIMIDE-4,5-DICARBOXYLIC ACIDS

[75] Inventors: Otto Fuchs, Frankfurt am Main; Adolf Kroh, Münster, Taunus, both of Fed. Rep. of Germany

[73] Assignee: Hoechst Aktiengesellschaft, Frankfurt am Main, Fed. Rep. of Germany

[21] Appl. No.: 739,277

[22] Filed: Nov. 5, 1976

Related U.S. Application Data

[60] Continuation-in-part of Ser. No. 505,624, Sep. 13, 1974, Pat. No. 4,007,192, which is a division of Ser. No. 398,410, Sep. 18, 1973, abandoned.

[30] Foreign Application Priority Data

Sep. 20, 1972 [DE] Fed. Rep. of Germany ....... 2246111

[51] Int. Cl.$^2$ ............................................. C07D 221/14
[52] U.S. Cl. .............................. 260/281 A; 260/281 F
[58] Field of Search ........................ 260/281 F, 281 A

[56] References Cited

U.S. PATENT DOCUMENTS

| | | | |
|---|---|---|---|
| 1,924,090 | 8/1933 | Eckert et al. | 260/281 A |
| 1,935,945 | 11/1933 | Eckert et al. | 260/281 A |
| 2,835,674 | 5/1958 | Eckert et al. | 260/281 |

FOREIGN PATENT DOCUMENTS

| | | |
|---|---|---|
| 1,147,702 | 5/1965 Fed. Rep. of Germany | 260/281 |
| 1,955,070 | 5/1971 Fed. Rep. of Germany. | |
| 2,246,110 | 4/1974 Fed. Rep. of Germany | 260/281 A |
| 2,246,111 | 4/1974 Fed. Rep. of Germany | 260/281 A |

OTHER PUBLICATIONS

Gerasimenko et al., "Chemical Abstracts," vol. 69 (1967), col. 51997n.

*Primary Examiner*—Donald G. Daus
*Assistant Examiner*—James H. Turnipseed
*Attorney, Agent, or Firm*—Curtis, Morris & Safford

[57] ABSTRACT

Naphthalimide-4,5-dicarboxylic acids of the formula

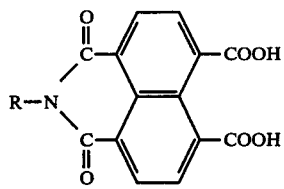

(I)

or the anhydrides thereof, wherein R is alkyl having 1 to 8 carbon atoms or hydroxyalkyl or alkoxyalkyl having each 1 to 6 carbon atoms in the alkyl or alkoxy portion, which are obtained by reacting an alkali metal salt of naphthalene-1,4,5,8-tetracarboxylic acid in an aqueous solution with amines of the formula $$H_2N - R \qquad (II)$$

wherein R has the above meaning, at a pH-value of 5.2 to 7.5 and at temperatures of 80° to 160° C, are intermediates for disperse dyestuffs.

5 Claims, No Drawings

NAPHTHALIMIDE-4,5-DICARBOXYLIC ACIDS

This is a continuation-in-part of our prior application Ser. No. 505,624, filed on Sept. 13, 1974, now U.S. Pat. No. 4,007,192 which in turn is a divisional application of our prior application Ser. No. 398,410, filed on Sept. 18, 1973, and now abandoned.

The preparation of two naphthalimide-4,5-dicarboxylic acids is known from German Pat. No. 553,629 and German Offenlegungsschrift No. 2,000,623.

Thus, Example 7 of German Pat. No. 553,629 describes the preparation of N-phenyl-naphthalimide-4,5-dicarboxylic acid by dissolving naphthalene-1,4,5,8-tetracarboxylic acid in water with the aid of potassium carbonate and heating it to the boil for some time together with aniline. However, the reaction is not complete. On testing this process it has appeared that the N-phenyl-naphthalimide-4,5-dicarboxylic acid, when acidified carefully, is not precipitated in pure form, but in mixture with the potassium salt thereof. The presence of rather large portions of potassium salt in the mixture explains that the melting point of the reaction product could not exactly be measured. The pure acid, however, melts at 318° C. If instead of aniline according to this Example other amines are used in equivalent amounts, the reaction is not quantitative either, and an expensive working-up to obtain the imide and to recover the naphthalene-tetracarboxylic acid not reacted is required.

Furthermore, it is known from German Pat. No. 1,005,969 that naphthalene-tetracarboxylic acid can be reacted in an aqueous solution in the presence of large amounts of buffer substances and salts with ortho-phenylene-diamines to give the corresponding naphthoylene-arylimidazol-peri-dicarboxylic acids. This known process is carried out with large amounts of liquid. Furthermore, the condensation products crystallizing during the reaction are not obtained in a completely pure form and their purification and conversion into the free acid require an expensive working-up. If the principle of this known process, which is limited to the reaction with orthodiamines, is applied to mono-amines, the reaction to give the corresponding imides is not quantitative under the conditions indicated therein. Due to the high salt concentration the products obtained are mostly precipitated so that they cannot be applied directly for the purpose mentioned below and would have to be subject also to a previous expensive working-up.

From German Offenlegungsschrift No. 2,000,623 it is known that N,N-dimethyl-1,3-diamino-propane can be condensed with naphthalene-tetracarboxylic acid or the anhydride thereof either in about 30 times the amount of dimethyl formamide or in 30 times the amount of water, to give the corresponding mono-imide. With the process carried out in dimethyl formamide the yield is only about 53% of the theory. Furthermore, the process has the disadvantage that large amounts of organic solvents must be used. The process carried out in water which essentially corresponds to Example 1 of German Pat. No. 1,005,969, with the difference that instead of the ortho-phenylene-diamine the corresponding amount of N,N-dimethyl-1,3-diamino-propane is used, has the same disadvantages described above. The monoimide is separated as hydrochloride with a yield of only about 77% of the theory.

In the amended specification of British Pat. No. 364,544 (which corresponds to German Pat. No. 553,629 discussed above) the preparation of naphthalene tetracarboxylic acid mono-ortho-toluidide and mono-para-chloroanilide is described. In this process naphthalene tetracarbocylic acid anhydride is transformed into its alkali metal salt which is reacted in water with the aromatic amine under addition of glacial acetic acid. From the so-obtained mixture of mono- and bis-imides the mono-imide is extracted with aqueous sodium carbonate solution and separated as the free acid by acidification. When trying to carry out this process with a non-aromatic amine, however, the product still contains a considerable amount of naphthalene tetracarboxylic acid.

The present invention relates to a naphthalimide-4,5-dicarboxylic acid of the formula

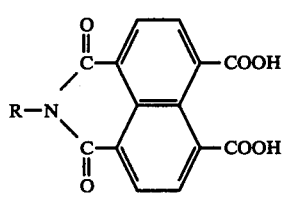
(I)

or the anhydride thereof, wherein R is alkyl having 1 to 8 carbon atoms or hydroxyalkyl or alkoxyalkyl having each 1 to 6, preferably 1 to 4 carbon atoms in each alkyl or alkoxy portion.

These compounds are obtained by reacting an alkali metal salt of naphthalene-1,4,5,8-tetracarboxylic acid in an aqueous solution with an amine of the formula $$H_2N - R \qquad (II)$$

wherein R has the above meaning, at a pH-value of 5.2 – 7.5, preferably of 5.4 – 6.4, at temperatures of 80° to 160° C.

These compounds can be prepared in a simple way by suspending 1 mol of the 1,4,5,8-naphthalene-tetracarboxylic acid, generally available as a semi-anhydride, in 12 to 20 times the amount of water, heating the suspension to 60° – 95° C and dissolving the naphthalene-tetracarboxylic acid with the 2 to 6-molar amount of sodium or potassium hydroxide solution. Then the pH-value is adjusted to about 5.0 – 5.6 with phosphoric acid or acetic acid, and the calculated amount of the amine of the general formula R—NH$_2$ is added in a slight excess of up to 10%, the pH-value being adjusted to 5.2 – 7.5. Then the condensation reaction is carried out at an elevated temperature, either under reflux or in a closed reaction vessel at a temperature of preferably 100° to 135° C during 2 to 6 hours, preferably 3 to 5 hours. During this period the naphthalene-tetracarboxylic acid is reacted quantitatively with the amine. The condensation product obtained as alkali salt is easily soluble in the reaction solution in the heat and can be easily freed, by simple filtration, from the corresponding naphthalene-tetracarboxylic acid diimide undissolved and formed simultaneously in a small amount. By acidifying the clarified solution with mineral acid, filtering the deposit formed and subsequently drying, the corresponding naphthalimide-4,5-dicarboxylic acids are obtained in a pure form and in very high to practically quantitative yields.

The free naphthalimide-dicarboxylic acids can be converted in known manner into the corresponding anhydrides, for example by heating in a high-boiling solvent, such as trichloro-benzene or α-chloro-naphthalene, while distilling off the water set free in the heat. By rapid vatting in alkaline sodium dithionite solutions the imide anhydrides according to the invention show a characteristic pure blue vat color.

In the cases in which, during condensation, less well-soluble alkali salts are formed, which are no longer completely soluble in the reaction solution in the heat, the reaction solution is acidified with mineral acid and the imide-dicarboxylic acids precipitated are isolated. To separate from the unsoluble diimide which has also formed, the moist crude product is suspended in water, the imide-dicarboxylic acid is dissolved in the heat by addition of sodium carbonate solution and the diimide is separated by filtration. In the same way as described above the imide-dicarboxylic acid is isolated. In this working-up care must be taken that the pH-value of the solution is not considerably above 8.0 after addition of the soda solution, since the naphthalimide-4,5-dicarboxylic acids are saponified very easily to give the naphthalene-tetracarboxylic acid. This fact is unusual since most of the naphthalimides are very resistant to alkali in the heat and can be saponified only with difficulty.

Amines which are used for the condensation with naphthalene-tetracarboxylic acid are for example: straight-chain and branched alkyl amines such as methyl-, ethyl-, propyl-, butyl-, hexylamine, isopropyl-, isobutyl-, 2-ethyl-hexylamine; straight-chain and branched alkyl amines substituted by hydroxy and/or alkoxy groups, such as amino-ethanol, aminopropanol, 2-amino-i-butanol, methoxyethylamine, methoxypropylamine, ethoxypropylamine, isopropoxy-propylamine or n-butoxy-propylamine.

The naphthalimide-4,5-dicarboxylic acids are valuable intermediate products for the preparation of dyestuffs. They make possible without an intermediate isolation of the naphthalimide-4,5-dicarboxylic acids and an expensive purification, to prepare in a particularly economical way valuable dispersion dyestuffs, for example those of the naphthoylene-arylimidazol-peri-dicarboxylic acid imide series, for dyeing synthetic fibres on the basis of polyester, polyacrylonitrile, cellulose acetate as well as polyamide. These dyestuffs are obtained by reacting the mono-imides with a phenylene diamine, e.g. by heating the reactants for 5 hours to 95° – 100° C in glacial acetic acid. The so-obtained yellow to orange disperse dyestuffs have a high tinctorial strength and a very clear and pure shade (and are far superior in these respects to the dyestuffs obtained from naphthalene-tetracarboxylic acid-(3-dimethylamino-n-propyl)-imide known from German Offenlegungsschrift No. 1,995,070). For the preparation of such dyestuff it is of high significance that the mono-imide does not contain naphthalene-1,4,5,8-tetracarboxylic acid since this compound reacts with 2 mols of the o-phenylene diamine to form red impurities which lead to an impure shade of the yellow to orange disperse dyestuffs and deteriorates their fastness properties.

The process of the present invention provides in a very economical way high yields of naphthalimide-4,5-dicarboxylic acids, which are free from naphthalene-tetra-carboxylic acid.

According to the state of the art it has been surprising that, when maintaining determined pH-conditions, a quantitative reaction of naphthalene-tetracarboxylic acid takes place in an aqueous solution with mono-amines.

The following Examples illustrate the invention.

EXAMPLE 1

20 Grams of naphthalene-1,4,5,8-tetracarboxylic acid-semianhydride were suspended in 300 ml of water and stirred at 70° C with 34 g of a 33% sodium hydroxide solution. After 10 minutes a pH-value of 5.1 to 5.3 was adjusted with 10.65 g of a 80% phosphoric acid; after addition of 6.6 g of 3-methoxy-n-propyl-amine the solution obtained had a pH-value of 5.9 to 6.1. The reaction solution was heated for 3 hours to 125° – 130° C. By filtration at 60° to 80° C the naphthalene-tetracarboxylic acid diimide formed in small amounts was separated, the filtrate was adjusted with hydrochloric acid to a pH-value of 2 and stirred for 30 minutes at 80° C. The N-(3′-methoxy-n-propyl)-naphthalimide-4,5-dicarboxylic acid precipitated was suction-filtered in the cold, washed free from salt with cold water and dried.

Yield: 94% of the theory.

To convert into the anhydride 15 g of the imide-dicarboxylic acid obtained were suspended in 150 g of α-chloro-naphthalene; the suspension was heated up to 250° C and allowed to stand for 5 hours at this temperature, while stirring. After cooling, the crystalline, nearly colorless N-(3′-methoxy-n-propyl)-naphthalimide-4,5-dicarboxylic acid anhydride was suction-filtered, washed with benzene and dried.

Melting point: 214° C.

EXAMPLE 2

If — in analogy to Example 1 — naphthalene-1,4,5,8-tetracarboxylic acid-semianhydride was reacted with 5.4 g of isobutyl-amino instead of with 3-methoxy-n-propylamine, the N-isobutyl-naphthalimide-4,5-dicarboxylic acid was obtained in a yield of 96% of the theory.

The melting point of the anhydride prepared according to the process of Example 1 was at 257° C.

EXAMPLE 3

In analogy to the method described in Example 1, the N-(3′-butoxy-n-propyl)-naphthalimide-1,4,5,8-dicarboxylic acid was obtained in a yield of 90% of the theory by reaction of 20 g of naphthalene-1,4,5,8-tetracarboxylic acid-semianhydride with 10.4 g of 3-butoxy-n-propylamine.

Melting point of the anhydride: 149° C.

EXAMPLE 4

50 Grams of naphthalene-1,4,5,8-tetracarboxylic acid semianhydride were suspended in 1000 ml of water; at 95° C this suspension was mixed with 42.5 g of a 33% sodium hydroxide solution and stirring was continued for 30 minutes. 16.5 Grams of 3-methoxy-n-propylamine and 3 g of phosphoric acid (85%) were added, and a pH-value of 5.7 to 5.8 was adjusted. The solution obtained was heated for 5 hours in a closed vessel, while stirring at 125° to 130° C. After cooling to 70° – 80° C it was filtered from the naphthalene-tetracarboxylic acid-di-(N-methoxy-propyl)-imide formed in only small amounts, the filtrate was adjusted to pH 1.5 – 2.0 with hydrochloric acid and stirring was continued for 30 minutes at 80° C.

The N-(3′-methoxy-n-propyl)-naphthalimide-4,5-dicarboxylic acid precipitated was suction-filtered in the cold, washed free from salt with cold water and dried.

Yield: 94% of the theory.

Melting point of the anhydride: 214° C.

EXAMPLE 5

106 Grams of naphthalene-1,4,5,8-tetracarboxylic acid were suspended in 1500 ml of water at 80° C and dissolved by addition of 170 g of a 33% sodium hydroxide solution. Then 48 g of glacial acetic acid were added while stirring, and stirring was continued for 10 minutes. After addition of 33 g of 3-methoxy-n-propylamine a pH-value of 5.8 was adjusted and the reaction solution was heated for 5 hours to 125° - 130° C. The N-(3'-methoxy-n-propyl)-naphthalimide-4,5-dicarboxylic acid was isolated as in Example 4.

Yield: 93% of the theory.
Melting point of the anhydride: 214° C.

EXAMPLE 6

50 Grams of naphthalene-1,4,5,8-tetracarboxylic acid-semianhydride were suspended in 750 ml of water and dissolved at 80° C by addition of 98 g of a 40% by weight solution of potash. After addition of 25 g of phosphoric acid (85% by weight) and 16.5 g of 3-methoxy-n-propylamine, a pH-value of 5.8 to 6.1 was adjusted; the solution was heated to 130° C and stirred for 5 hours at this temperature. After cooling to 90° C, the potassium salt, partly precipitated, of the N-(3'-methoxy-propyl)-naphthalimide-4,5-dicarboxylic acid was adjusted to an acidic range with hydrochloric acid; the stirring of the solution was continued for 30 minutes at 80° - 90° C. The crystalline precipitation 10suction-filtered in the cold and washed free from salt with water.

The moist press-cake was dissolved in 700 ml of water at 70° C with a 10 % sodium carbonate solution and the solution obtained had a pH-value of about 7.0 to 7.5. The naphthalene-tetracarboxylic acid-di-(methoxy-propyl)-imide undissolved and formed in small amounts was separated by filtration. The filtrate was adjusted to pH 2 with hydrochloric acid, and stirring was continued at 70° - 80° C for 30 minutes. The N-(3'-methoxy-n-propyl)-naphthalimide-4,5-dicarboxylic acid precipitated was suction-filtered cold, washed free from salt with cold water and dried.

Yield: 94% of the theory.
Melting point of the anhydride: 214° C.

EXAMPLES 7 and 8

50 Grams of naphthalene-1,4,5,8-tetracarboxylic acid-semianhydride were dissolved in 750 ml of water with the aid of 82 g of a 33% sodium hydroxide solution at 80° C. The solution was mixed with 20 g of a 85% phosphoric acid and the calculated amount of amine given in the following table, a pH-value of 6.4 being adjusted. The solution was heated to 130° C in a closed vessel and maintained for about 5 hours at this temperature. After cooling to 60° - 80° C, the undissolved naphthalene-tetracarboxylic acid-diimide formed was separated by filtration; the filtrate was adjusted to pH 2 with hydrochloric acid and stirred for 30 minutes at about 80° C. The naphthalimide-4,5-dicarboxylic acid formed was suction-filtered after cooling the solution, washed free from salt and dried. The products had a high purity.

Yield: More than 90% of the theory.

TABLE

| Example | Amine | Final Product | Melting Point ° C |
|---|---|---|---|
| 7 | $NH_2-CH_3$ | N-methyl-naphthalimide-4,5-dicarboxylic acid | 367 (Anhydride) |
| 8 | $CH_3-(CH_2)_4-CH_2-NH_2$ | N-n-hexyl-naphthalimide-4,5-dicarboxylic acid | 180 (Anhydride) |

We claim:
1. A compound of the formula

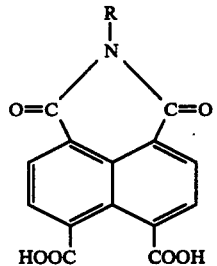

or the anhydride thereof, wherein R is alkoxyalkyl having 1 to 6 carbon atoms in each of the alkyl and alkoxy portions.

2. A compound as claimed in claim 1, wherein R is alkoxyalkyl having each 1 to 4 carbon atoms in the alkyl or alkoxy portion.

3. The compound as claimed in claim 1, wherein R is 3-butoxy-n-propyl.

4. The compound as claimed in claim 1, wherein R is 3-methoxy-n-propyl.

5. A naphthalimide-4,5-dicarboxylic acid of the formula

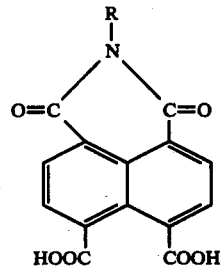

or the anhydride thereof wherein R is 3-butoxy-n-propyl or 3-methoxy-n-propyl.

* * * * *